US011939282B2

(12) United States Patent
Kang et al.

(10) Patent No.: US 11,939,282 B2
(45) Date of Patent: *Mar. 26, 2024

(54) METHOD FOR DECOMPOSING PHENOLIC BY-PRODUCT

(71) Applicant: LG CHEM, LTD., Seoul (KR)

(72) Inventors: Min Suk Kang, Daejeon (KR); Sang Beom Lee, Daejeon (KR); Joon Ho Shin, Daejeon (KR)

(73) Assignee: LG Chem, Ltd., Seoul (KR)

(*) Notice: Subject to any disclaimer, the term of this patent is extended or adjusted under 35 U.S.C. 154(b) by 366 days.

This patent is subject to a terminal disclaimer.

(21) Appl. No.: 17/413,790

(22) PCT Filed: Aug. 11, 2020

(86) PCT No.: PCT/KR2020/010599
§ 371 (c)(1),
(2) Date: Jun. 14, 2021

(87) PCT Pub. No.: WO2021/054607
PCT Pub. Date: Mar. 25, 2021

(65) Prior Publication Data
US 2022/0009868 A1 Jan. 13, 2022

(30) Foreign Application Priority Data
Sep. 16, 2019 (KR) ........................ 10-2019-0113587

(51) Int. Cl.
*C07C 37/76* (2006.01)
*B01D 17/02* (2006.01)
(Continued)

(52) U.S. Cl.
CPC .............. *C07C 37/76* (2013.01); *B01D 17/02* (2013.01); *C07C 37/005* (2013.01); *C07C 37/72* (2013.01); *B01D 2257/70* (2013.01)

(58) Field of Classification Search
None
See application file for complete search history.

(56) References Cited

U.S. PATENT DOCUMENTS

| 4,158,611 | A | | 6/1979 | Cooke |
| 5,504,251 | A | * | 4/1996 | Dyckman ............... C07C 37/52 568/749 |

(Continued)

FOREIGN PATENT DOCUMENTS

| EP | 3715338 A1 | 9/2020 |
| JP | 9-110766 A | 4/1997 |

(Continued)

*Primary Examiner* — Renee Robinson
(74) *Attorney, Agent, or Firm* — Bryan Cave Leighton Paisner LLP (57) ABSTRACT

The present disclosure provides a method for decomposing a phenolic by-product, the method including: a step S10 of injecting and mixing a bisphenol A by-product produced in a bisphenol A production process, a mixed by-product stream of phenol by-products produced in a phenol production process, a decomposition apparatus side discharge stream, and a process water stream in a mixing apparatus; a step S20 of injecting a mixing apparatus discharge stream discharged from the mixing apparatus into a phase separation apparatus and phase-separating the mixing apparatus discharge stream into an oil-phase stream and a liquid-phase stream; a step S30 of feeding the oil-phase stream, which is phase-separated in the step S20 and discharged from the phase separation apparatus, to a decomposition apparatus to decompose the oil-phase stream; and a step S40 of circulating the decomposition apparatus side discharge stream obtained by the decomposition in the step S30 to the mixing apparatus in the step S10.

10 Claims, 2 Drawing Sheets

(51) Int. Cl.
   *C07C 37/00*   (2006.01)
   *C07C 37/72*   (2006.01)

(56) References Cited

U.S. PATENT DOCUMENTS

| | | |
|---|---|---|
| 5,510,543 A | 4/1996 | Fulmer et al. |
| 2001/0000260 A1 | 4/2001 | Taggart, II et al. |

FOREIGN PATENT DOCUMENTS

| | | |
|---|---|---|
| JP | 2005-29478 A | 2/2005 |
| JP | 2011-500831 A | 1/2011 |
| JP | 2012-506905 A | 3/2012 |
| JP | 5661466 B2 | 12/2014 |
| JP | 6302058 B2 | 3/2018 |
| KR | 10-0396718 B1 | 12/2003 |
| KR | 10-0843003 B1 | 7/2008 |
| KR | 10-2011-0081873 A | 7/2011 |
| KR | 10-2014-0037086 A | 3/2014 |
| KR | 10-2014-0138325 A | 12/2014 |
| KR | 10-2019-0058273 A | 5/2019 |
| WO | 2020130313 A1 | 6/2020 |

* cited by examiner

METHOD FOR DECOMPOSING PHENOLIC BY-PRODUCT

CROSS-REFERENCE TO RELATED APPLICATIONS

The present application is a National Phase entry pursuant to 35 U.S.C. § 371 of International Application No. PCT/KR2020/010599, filed on Aug. 11, 2020, and claims the benefit of and priority to Korean Patent Application No. 10-2019-0113587, filed on Sep. 16, 2019, the disclosure of which are incorporated by reference in their entirety for all purposes as if fully set forth herein.

TECHNICAL FIELD

The present invention relates to a method for decomposing a phenolic by-product, and more particularly, to a method for decomposing a mixed by-product of bisphenol A by-product produced in a bisphenol A production process and a phenol by-product produced in a phenol production process.

BACKGROUND ART

In general, about 95% of phenol used in the world is produced by a Hock process. The Hock process is performed in three steps including: a step (1) of forming cumene by alkylation of benzene with propylene, a step (2) of oxidizing the cumene to cumene hydroperoxide (CHP) by combining the cumene and oxygen, and a step (3) of decomposing the cumene hydroperoxide into phenol and acetone by an acid decomposition reaction in the presence of an acid catalyst.

Here, in the cumene oxidation step which is the step (2), by-products such as acetophenone (AP), dimethyl benzyl alcohol (DMBA), dicumylperoxide (DCP), and dicumene (DC) are produced in addition to cumene hydroperoxide.

In addition, in the acid decomposition reaction of the cumene hydroperoxide in the step (3), by-products such as hydroxy acetone (HA), 2-methylbenzofuran (2-MBF), alpha-methyl styrene (AMS), mesityl oxide (MO), alpha-methyl styrene (AMS) dimer, and cumylphenol (CP) are produced in addition to phenol and acetone.

Accordingly, since a product stream produced in such a reaction process is present in a state in which phenol, acetone, and various by-products are mixed with each other, a separation process for separating the phenol from the product stream is required.

The product stream is injected into a separate separation apparatus, an acetone-based mixture including unreacted cumene, acetone, alpha-methyl styrene, hydroxy acetone, and the like is separated through a top of the separation apparatus, and a phenolic mixture including phenol, a part of alpha-methyl styrene, 2-methylbenzofuran, and other by-products is separated through a bottom of the separation apparatus.

The phenolic mixture separated through the bottom of the separation apparatus is injected into a phenol column, phenol is separated through a top of the phenol column, and phenolic by-products such as dicumylperoxide, cumylphenol, alpha-methyl styrene dimer, and tar are separated through a bottom of the phenol column.

In addition, in general, a process of producing bisphenol A (BPA) is a process of producing bisphenol A by a condensation reaction between the phenol and the acetone produced in the Hock process in the presence of an acid catalyst or a cation exchange resin.

As a result, by-products such as unreacted phenol, unreacted acetone, trisphenol (BPX), and tar are produced in the product stream produced by the bisphenol A reaction in addition to bisphenol A.

Active ingredients such as phenol, cumene, and alpha-methyl styrene may be recovered from the by-products produced in the phenol production process and the bisphenol A production process by a separate separation apparatus. Studies on a decomposition process and a decomposition apparatus that are capable of effectively recovering active ingredients have been conducted.

Disclosure

Technical Problem

In order to solve the problems mentioned in the background art, an object of the present invention is to obtain a high value-added active ingredient while reducing a process cost by simultaneously decomposing by-products produced in a phenol production process and a bisphenol A production process when decomposing a mixed by-product of a bisphenol A by-product produced in the bisphenol A production process and a phenol by-product produced in the phenol production process to obtain an active ingredient.

That is, an object of the present invention is to provide a method for decomposing a phenolic by-product capable of effectively removing a salt included in a phenolic mixed by-product prior to decomposition of a mixed by-product, effectively obtaining an active ingredient by decomposing a phenolic by-product, and reducing process energy by preventing a load in a phenol production process.

Technical Solution

In one general aspect, a method for decomposing a phenolic by-product includes: a step S10 of injecting and mixing a mixed by-product stream of a bisphenol A by-product produced in a bisphenol A production process and a phenol by-product produced in a phenol production process, a decomposition apparatus side discharge stream, and a process water stream into and in a mixing apparatus; a step S20 of injecting a mixing apparatus discharge stream discharged from the mixing apparatus into a phase separation apparatus and phase-separating the mixing apparatus discharge stream into an oil-phase stream and a liquid-phase stream; a step S30 of feeding the oil-phase stream phase-separated in the step S20 and discharged to a decomposition apparatus to decompose the oil-phase stream; and a step S40 of circulating a decomposition apparatus side discharge stream obtained by the decomposition in the step S30 to the mixing apparatus in the step S10.

Advantageous Effects

In a case where the mixed by-product of the bisphenol A by-product produced in the bisphenol A production process and the phenol by-product produced in the phenol production process is decomposed according to the method for decomposing a phenolic by-product according to the present invention, the salt included in the phenolic by-product can be effectively removed prior to the decomposition of the phenolic by-product, such that the active ingredient can be effectively obtained by decomposing the phenolic by-product and a content of acetophenone in the active ingredient can be reduced.

Further, in a case where the mixed by-product of the bisphenol A by-product produced in the bisphenol A production process and the phenol by-product produced in the phenol production process is decomposed according to the method for decomposing a phenolic by-product according to the present invention, the process energy can be reduced.

DETAILED DESCRIPTION

The terms and words used in the description and claims of the present invention are not to be construed as general or dictionary meanings but are to be construed as meanings and concepts meeting the technical ideas of the present invention based on a principle that the inventors can appropriately define the concepts of terms in order to describe their own inventions in best mode.

The term "stream" in the present invention may refer to a flow of a fluid in a process, and may also refer to a fluid flowing through a pipe itself. Specifically, the "stream" may refer to both the fluid flowing through the pipe connecting respective apparatuses to each other itself and the flow of the fluid at the same time. In addition, the fluid may refer to gas.

Hereinafter, the present invention will be described in more detail with reference to FIG. 1 in order to assist in the understanding of the present invention.

According to an exemplary embodiment of the present invention, a method for decomposing a phenolic by-product can include: a step S10 of injecting and mixing a mixed by-product of a bisphenol A by-product produced in a bisphenol A production process and a phenol by-product produced in a phenol production process, a decomposition apparatus 300 side discharge stream, and process water stream in a mixing apparatus 100; a step S20 of injecting a mixing apparatus 100 discharge stream discharged from the mixing apparatus 100 into a phase separation apparatus 200 and phase-separating the mixing apparatus 100 discharge stream into an oil-phase stream and a liquid-phase stream; a step S30 of feeding the oil-phase stream phase-separated in the step S20 and discharged to a decomposition apparatus 300 to decompose the oil-phase stream; and a step S40 of circulating a decomposition apparatus 300 side discharge stream obtained by the decomposition in the step S30 to the mixing apparatus 100 in the step S10.

According to an exemplary embodiment of the present invention, the phenol production process can be performed through the Hock process described above.

Specifically, the phenol production process can be performed through a step of decomposing and purifying cumene hydroperoxide produced by an oxidation reaction of cumene to separate the cumene hydroperoxide into phenol and acetone. The step of decomposing and purifying the cumene hydroperoxide produced by the oxidation reaction of the cumene to separate the cumene hydroperoxide into the phenol and the acetone is a step using a cumene purification process and a phenol/acetone purification process. In this step, first, cumene is produced by an alkylation reaction between propylene and benzene, heavy/light by-products are discharged through a purification process, and the cumene is purified and separated. Subsequently, cumene hydroperoxide (CHP) is produced by an oxidation reaction of the purified cumene, phenol, acetone, α-methyl styrene (AMS), and heavy by-products are produced by a decomposition reaction of the cumene hydroperoxide (CHP) in the presence of a general acid catalyst such as sulfuric acid ($H_2SO_4$), and the α-methyl styrene (AMS) and the heavy by-products are discharged and the phenol and the acetone are purified and separated through a purification process.

Since a product stream produced in such a reaction process is present in a state in which phenol, acetone, and various by-products are mixed with each other, a separation process for separating the phenol from the product stream is required.

The product stream is injected into a separate separation apparatus, an acetone-based mixture including unreacted cumene, acetone, alpha-methyl styrene, hydroxy acetone, and the like is separated through a top of the separation apparatus, and a phenolic mixture including phenol, a part of alpha-methyl styrene, 2-methylbenzofuran, and other by-products is separated through a bottom of the separation apparatus.

The phenolic mixture separated through the bottom of the separation apparatus is injected into a phenol column, phenol is separated through a top of the phenol column, and phenolic by-products such as dicumylperoxide, cumylphenol, alpha-methyl styrene dimer, and tar are separated through a bottom of the phenol column.

As a result, the phenol by-product produced in the phenol production process can include some active ingredients such as phenol, cumene, and alpha-methyl styrene, and tar.

According to an exemplary embodiment of the present invention, the bisphenol A production process can be performed by a method of producing bisphenol A by a reaction between the phenol and the acetone produced in the Hock process described above and recovering the bisphenol A from the reaction product.

Specifically, the bisphenol A production process can be performed through a step of decomposing and purifying cumene hydroperoxide produced by an oxidation reaction of cumene to separate the cumene hydroperoxide into phenol and acetone; a step of separating bisphenol A produced by a reaction between the separated phenol and acetone and decomposing a stream including unseparated bisphenol A in an aqueous alkaline solution; and a step of separating a reaction product, a phenolic by-product, and an acetone-based by-product obtained by the decomposition reaction.

The step of decomposing and purifying the cumene hydroperoxide produced by the oxidation reaction of the cumene to separate the cumene hydroperoxide into the phenol and the acetone is a step using a cumene purification process and a phenol/acetone purification process. In this step, first, cumene is produced by an alkylation reaction between propylene and benzene, heavy/light by-products are discharged through a purification process, and the cumene is purified and separated. Subsequently, cumene hydroperoxide (CHP) is produced by an oxidation reaction of the purified cumene, phenol, acetone, α-methyl styrene (AMS), and heavy by-products are produced by a decomposition reaction of the cumene hydroperoxide (CHP) in the presence of a general acid catalyst such as sulfuric acid ($H_2SO_4$), and the α-methyl styrene (AMS) and the heavy by-products are discharged and the phenol and the acetone are purified and separated through a purification process.

The step of separating the bisphenol A produced by the reaction between the separated phenol and acetone and decomposing the stream including the unseparated bisphenol A in the aqueous alkaline solution is a step using a bisphenol A (BPA) purification process. In this step, first, bisphenol A, more specifically, crude bisphenol A is produced by a reaction between the purified and separated phenol and acetone, and then bisphenol A with improved purity is produced via a crystallization process. The produced bisphenol A is separated via the BPA purification process, and a by-product stream including the unseparated bisphenol A is decomposed in an excessive amount of an aqueous alkaline solution having basic properties such as NaOH, KOH, or LiOH.

In the step of separating the reaction product, the phenolic by-product, and the acetone-based by-product obtained by the decomposition reaction, a stream in which the decomposition reaction is completed can be fed to the decomposition apparatus, the acetone-based mixture can be separated through the top of the separation apparatus, and the phenolic mixture can be separated through the bottom of the separation apparatus. The phenolic mixture is injected into the phenol column, phenol is separated through the top of the phenol column, and phenolic by-products such as dicumylperoxide, cumylphenol, alpha-methyl styrene dimer, and tar are separated through the bottom of the phenol column. In this case, the phenolic by-product includes some active ingredients such as bisphenol A, cumene, and alpha-methyl styrene which are products in addition to tar which is an impurity.

As a result, the bisphenol A by-product produced in the bisphenol A production process can include some active ingredients such as bisphenol A, phenol, cumene, and alpha-methyl styrene, and tar.

Therefore, the mixed by-product of the bisphenol A by-product produced in the bisphenol A production process and the phenol by-product produced in the phenol production process can include one or more selected from the group consisting of bisphenol A, phenol, alpha-methyl styrene, acetophenone, cumylphenol, and alpha-methyl styrene dimer, as a phenolic by-product. As a specific example, the mixed by-product can include two or more selected from the group consisting of bisphenol A, phenol, alpha-methyl styrene, acetophenone, cumylphenol, and alpha-methyl styrene dimer, or all of them.

In the mixed by-product, a flow rate ratio of the bisphenol A by-product to the phenol by-product can be 1:2 to 10. For example, in the mixed by-product, the flow rate ratio of the bisphenol A by-product to the phenol by-product can be 1:2 to 10, 1:4 to 10, or 1:6 to 10. As such, it is preferable that the mixed by-product in which a content of the phenol by-product is higher than that of the bisphenol A by-product is decomposed.

According to an exemplary embodiment of the present invention, the phenol production process and the bisphenol A production process can be performed by including the acid decomposition reaction of the cumene hydroperoxide described above. In this case, since the acid decomposition reaction of the cumene hydroperoxide is performed by including acid, an acid decomposition reaction solution contains acid. Therefore, in order to obtain phenol and acetone from the acid decomposition reaction solution through a process such as distillation, it is required to perform a process of neutralizing the acid decomposition reaction solution.

Prior to separation of the acid decomposition reaction solution, the acid decomposition reaction solution is neutralized by a basic aqueous solution or the like. In this case, in the neutralized acid decomposition reaction solution, a salt is generated by a neutralization reaction between the acid used in the acid decomposition reaction and the base in the basic aqueous solution or the like. A phase of the acid decomposition reaction solution neutralized by the neutralization process is separated into an oil phase and a liquid phase. A separation process for obtaining phenol and acetone from the separated oil phase is performed. In this case, the salt is mostly removed together with the liquid phase, but a part of the salt remains in the oil phase.

Such a salt remains in the phenol by-product and the bisphenol A by-product described in the present invention, that is, the mixed by-product of the bisphenol A by-product produced in the bisphenol A production process and the phenol by-product produced in the phenol production process. The salt remaining in the mixed by-product causes corrosion, occlusion, and deposition in the decomposition apparatus 300 when the mixed by-product is decomposed to obtain the active ingredient from the mixed by-product later, which causes a breakdown in the decomposition apparatus. Therefore, it is important to minimize the salt included in the mixed by-product when decomposing the mixed by-product including the phenolic by-products.

To this end, it is possible to consider a method of removing the salt by injecting process water prior to the decomposition of the mixed by-product as a method of removing the salt included in the mixed by-product; however, in this case, the phase separation into the oil phase and the liquid phase is not smoothly performed, and thus, the salt may not be sufficiently removed.

In addition, it is possible to consider a method of removing the salt by injecting organic matters such as cumene and alpha-methyl styrene discharged as active ingredients from an acetone column in the phenol production process to the mixed by-product together with process water; however, in this case, the cumene and the alpha-methyl styrene are required to be obtained again as a product, which causes an overload in the phenol production process and an increase in the entire operation energy.

In addition, it is possible to consider a method of removing the salt by injecting, to the mixed by-product, organic matters such as phenol, cumene, alpha-methyl styrene discharged as active ingredients through a top discharge stream of the decomposition apparatus 300 which decomposes the mixed by-product together with process water; however, in this case, since the top discharge stream of the decomposition apparatus 300 obtained as the active ingredient is used as it is, cold and hot energy is additionally required to operate a condenser provided above the decomposition apparatus 300 due to a reduction in purification efficiency and a reduction in stream to be circulated, and as a result, the entire operation energy is increased.

On the other hand, according to the method for decomposing a phenolic by-product according to the present invention, the salt included in the mixed by-product can be minimized, such that the operation of the decomposition apparatus 300 for the mixed by-product can be stably operated, thereby effectively obtaining the active ingredient by the decomposition of the mixed by-product.

According to an exemplary embodiment of the present invention, the step S10 can be a step for minimizing the salt included in the mixed by-product, and can be a step of injecting a decomposition apparatus 300 side discharge stream and a process water stream to be described below to the mixed by-product stream and performing mixing in the mixing apparatus 100, prior to direct supply of the mixed by-product stream including the phenolic by-products to the decomposition apparatus 300 as in the related art.

As described above, the mixed by-product stream can include one or more selected from the group consisting of bisphenol A, phenol, alpha-methyl styrene, acetophenone, cumylphenol, and alpha-methyl styrene dimer. As a specific example, the mixed by-product stream can include two or more selected from the group consisting of bisphenol A, phenol, alpha-methyl styrene, acetophenone, cumylphenol, and alpha-methyl styrene dimer, or all of them. These components can be components included in the phenolic by-product discharged in the process of separating the acetone-based mixture and the phenolic mixture from the acid decomposition reaction solution in the phenol production process by the separation apparatus and separating the phenol and the phenolic by-product from the phenolic mixture by the phenol column.

The decomposition apparatus 300 side discharge stream is a stream discharged from a side of a decomposition apparatus 300 to be described below, and can include one or more selected from the group consisting of phenol, acetophenone, isopropyl phenol, alpha-methyl styrene, and cumene. As a specific example, the decomposition apparatus 300 side discharge stream can include phenol, acetophenone, isopropyl phenol, alpha-methyl styrene, and cumene. The reason why the decomposition apparatus 300 side discharge stream is injected into the mixing apparatus 100 is to activate the phase separation into the oil phase and the liquid phase including the salt when the acetophenone included in the decomposition apparatus 300 side discharge stream is phase-separated in a step S20 to be described below, thereby minimizing the salt remaining in the oil phase.

In particular, the acetophenone can be included in the decomposition apparatus 300 side discharge stream in an amount of 20 wt % or more, 40 wt % or more, or 20 wt % to 99 wt %. The acetophenone is an organic matter included in the mixed by-product stream, and acts as an impurity when the active ingredient obtained by the decomposition reaction of the mixed by-product is used. Accordingly, it is preferable that a content of the acetophenone in the active ingredient is minimized. Therefore, when the acetophenone is included in the decomposition apparatus 300 side discharge stream in an amount of 20 wt % or more, 40 wt % or more, or 20 wt % to 99 wt % according to the present invention, the acetophenone can be used for removing the salt in the oil phase of the mixed by-product in the phase separation step S20, and the content of the acetophenone in the active ingredient obtained by the decomposition reaction of the mixed by-product can be minimized, which is advantageous in obtaining the active ingredient.

The decomposition apparatus 300 side discharge stream can include a residual phenol which is not separated from the phenol column and a part of the phenol obtained from the decomposition step S30 of the mixed by-product. In this regard, since a difference in boiling point between the phenol (boiling point: 181.7° C.) and the acetophenone (boiling point: 202° C.) is small and the phenol forms an azeotrope with the acetophenone, in a case where an operation temperature of the decomposition apparatus 300 is increased to obtain the phenol from the top of the decomposition apparatus 300 as much as possible, a part of the acetophenone can be included in the active ingredient together with the phenol and discharged.

Therefore, the method of decomposing a phenolic by-product according to the present invention can be performed by intentionally lowering a temperature below the operation temperature for obtaining the entire amount of the phenol from the top of the decomposition apparatus 300 to discharge the acetophenone through the decomposition apparatus 300 side discharge stream as much as possible. Accordingly, the phenol can be included in the decomposition apparatus 300 side discharge stream. As described above, the phenol included in the decomposition apparatus 300 side discharge stream is finally circulated to the mixing apparatus 100, and thus, the phenol can be continuously recovered from the decomposition apparatus 300 according to a circulation process.

As a specific example, the phenol can be included in the decomposition apparatus 300 side discharge stream in an amount of 1 wt % to 10 wt %, 1 wt % to 8 wt %, or 1 wt % to 7 wt % with respect to the mixed by-product stream. Within these ranges, a content of the salt included in the mixed by-product stream can be minimized, and the content of the acetophenone in a decomposition apparatus 300 top discharge stream can be minimized.

The process water is used for dissolving and removing the salt included in the mixed by-product stream, and may refer to various aqueous solutions such as an aqueous acidic solution and an aqueous basic solution as well as distilled water.

A pH of the process water can be 3.5 to 7, 3.5 to 5.5, or 3.5 to 4.5. Within these ranges, solubility of the salt can be improved while preventing corrosion of the mixing apparatus 100 and the phase separation apparatus 200, and separation ability when the phase separation into the oil phase and the liquid phase is performed in the phase separation apparatus 200 can be improved.

In addition, the process water can include process water derived from a liquid-phase aqueous solution separated in a step S20 to be described below. As a specific example, the process water can be supplied from a part of the liquid-phase aqueous solution separated in the step S20. In this case, the process water is used while being continuously circulated in the process during the decomposition of the mixed by-product, such that the amount of process water to be newly injected can be minimized.

According to an exemplary embodiment of the present invention, the mixing apparatus 100 in the step S10 can be a mixer for mixing the mixed by-product stream, the decomposition apparatus 300 side discharge stream, and the process water stream with each other. As a specific example, the mixer can be provided with a line mixer or a static mixer to easily perform the mixing of the mixed by-product stream, the decomposition apparatus 300 side discharge stream, and the process water stream.

According to an exemplary embodiment of the present invention, in the step S10, a flow rate ratio of the mixed by-product stream to the decomposition apparatus 300 side discharge stream can be 0.8 to 1.2:0.1 to 0.4. For example, the flow rate ratio of the mixed by-product stream to the decomposition apparatus 300 side discharge stream can be 1:0.1 to 0.4, 1:0.1 to 0.3, or 1:0.2 to 0.3. The mixed by-product stream and the decomposition apparatus 300 side discharge stream can be injected into the mixing apparatus 100 at a ratio of the above range and can be mixed with each other, such that the phase separation ability of the oil phase and the liquid phase in a step S20 to be described below can be improved, and salt removal efficiency can be improved.

According to an exemplary embodiment of the present invention, in the step S10, a flow rate ratio between the mixed by-product stream, the decomposition apparatus 300 side discharge stream, and the process water stream can be 0.8 to 1.2:0.1 to 0.4:0.8 to 1.5. For example, the flow rate ratio between the mixed by-product stream, the decomposition apparatus 300 side discharge stream, and the process water stream can be 1:0.1 to 0.4:0.8 to 1.5, 1:0.1 to 0.3:1 to 1.5, or 1:0.2 to 0.3:1.2 to 1.3. By controlling the flow rate ratio between the mixed by-product stream, the decomposition apparatus 300 side discharge stream, and the process water stream to the above range, not only the mixing of the mixed by-product stream, the decomposition apparatus 300 side discharge stream, and the process water stream but also the phase separation ability of the oil phase and the liquid phase in a step S20 to be described below can be improved, and the salt removal efficiency can be improved.

According to an exemplary embodiment of the present invention, the step S20 can be a step of removing the salt from the mixing apparatus 100 discharge stream discharged from the mixing apparatus 100, injecting the mixing apparatus 100 discharge stream into the phase separation apparatus 200 to inject the mixing apparatus 100 discharge stream into the decomposition apparatus 300, and phase-separating the mixing apparatus 100 discharge stream into the oil-phase stream and the liquid-phase stream.

The oil-phase stream phase-separated in the phase separation apparatus 200 and discharged is a stream obtained by removing the salt from the mixed by-product stream in the step S10 and the step S20, and can be used as a feed stream of the decomposition apparatus 300. In the decomposition apparatus 300 using the oil-phase stream as the feed stream, since the content of the salt in the feed stream is minimized, when the mixed by-product is decomposed, the corrosion, occlusion, and deposition in the decomposition apparatus 300 can be prevented.

In addition, the liquid-phase stream phase-separated in the phase separation apparatus 200 and discharged can include the salt. Therefore, the salt can be removed from the mixed by-product. Meanwhile, as described above, a part of the liquid-phase stream can be re-fed as the process water in the step S10.

The phase separation apparatus 200 in the step S20 can be a drum for separating the mixing apparatus 100 discharge stream into an oil phase and a liquid phase.

For the phase separation into the oil phase and the liquid phase, the step S20 can include a step of leaving a phase separation solution derived from the mixing apparatus 100 discharge stream in the phase separation apparatus 200 for 1 hour to 10 hours, 2 hours to 8 hours, or 3 hours to 5 hours. As such, in a case where the phase separation solution is left in the phase separation apparatus 200, the phase separation can be more completely performed, and thus, the salt can be removed from the liquid phase as much as possible.

According to an exemplary embodiment of the present invention, the step S30 can be a step of feeding the oil-phase stream phase-separated in the step S20 and discharged, that is, the mixed by-product in which the content of the salt is minimized to the decomposition apparatus 300 to decompose the oil-phase stream.

The decomposition performed in the decomposition apparatus 300 can be thermal cracking, and the decomposition apparatus 300 for performing this can be a thermal cracker. As a specific example, the thermal cracker can be a reactor-distillation tower integrated type separation apparatus.

As described above, the decomposition in the step S30 can be performed by intentionally lowering the temperature below the operation temperature for obtaining the entire amount of the phenol from the top of the decomposition apparatus 300 to discharge the acetophenone through the decomposition apparatus 300 side discharge stream as much as possible. For example, the decomposition in the step S30 can be performed at 260° C. to 370° C., 290° C. to 370° C., or 300° C. to 350° C. Within these ranges, the acetophenone is discharged through the decomposition apparatus 300 side discharge stream as much as possible, which is effective in minimizing the content of the acetophenone in the decomposition apparatus 300 top discharge stream.

The decomposition in the step S30 can be performed at 0.1 bar to 3.0 bar, 0.1 bar to 2.0 bar, or 0.1 bar to 1.5 bar in order to separate the components in the decomposition apparatus 300 side discharge stream and the decomposition apparatus 300 top discharge stream. In this case, the operation temperature of the decomposition apparatus 300 can be kept at a low temperature, and dimerization or polymerization of the alpha-methyl styrene in the active ingredient included in the decomposition apparatus 300 top discharge stream can be prevented. In addition, the operation temperature can be kept at a low temperature, such that the thermal energy required for the operation of the decomposition apparatus 300 can be reduced.

The decomposition apparatus 300 can be a multi-stage decomposition apparatus, and in this case, the decomposition apparatus 300 side discharge stream can be discharged at a middle position (corresponding to 25% to 90%, 40% to 90%, or 50% to 90% of the total stages) of the side of the decomposition apparatus 300. In this case, the amount of the acetophenone discharged through the decomposition apparatus 300 top discharge stream can be significantly reduced.

The decomposition apparatus 300 top discharge stream obtained by the decomposition in the step S30 can include one or more selected from the group consisting of phenol, alpha-methyl styrene, and cumene, as the active ingredients. The active ingredient can include the phenol which is not separated at the bottom of the phenol column and is included in the mixed by-product stream and the phenol which is decomposed in the decomposition step S30 and is discharged through the decomposition apparatus 300 top discharge stream. In addition, the active ingredient can include useful components which can be additionally used (for example, alpha-methyl styrene, cumene, and the like) and useful components which are decomposed in the decomposition step S30 and discharged through the decomposition apparatus 300 top discharge stream in addition to the phenol, among the components separated at the bottom of the phenol column and included in the mixed by-product stream. That is, the active ingredient can refer to a component decomposed in the decomposition step S30 and discharged through the decomposition apparatus 300 top discharge stream.

A decomposition apparatus 300 bottom discharge stream discharged by the decomposition in the step S30 can be recovered as tar and can be reused as a fuel or the like.

According to an exemplary embodiment of the present invention, the step S40 can be a step of circulating a decomposition apparatus 300 side discharge stream obtained by the decomposition in the step S30 to the mixing apparatus 100 in the step S10 so as to remove the salt included in the mixed by-product stream. As described above, according to the present invention, in a case where the decomposition apparatus 300 side discharge stream is circulated to the mixing apparatus 100 in the step S10, the phase separation into the oil phase and the liquid phase including the salt is activated during the phase separation in the step S20, such that the salt remaining in the oil phase can be minimized.

Hereinafter, the present invention will be described in more detail by examples. However, the following examples are provided for illustrating the present invention. It is apparent to a person skilled in the art that various modifications and alterations may be made without departing from the scope and spirit of the present invention, and the scope of the present invention is not limited thereto.

EXAMPLE

Example 1

Figure 1:
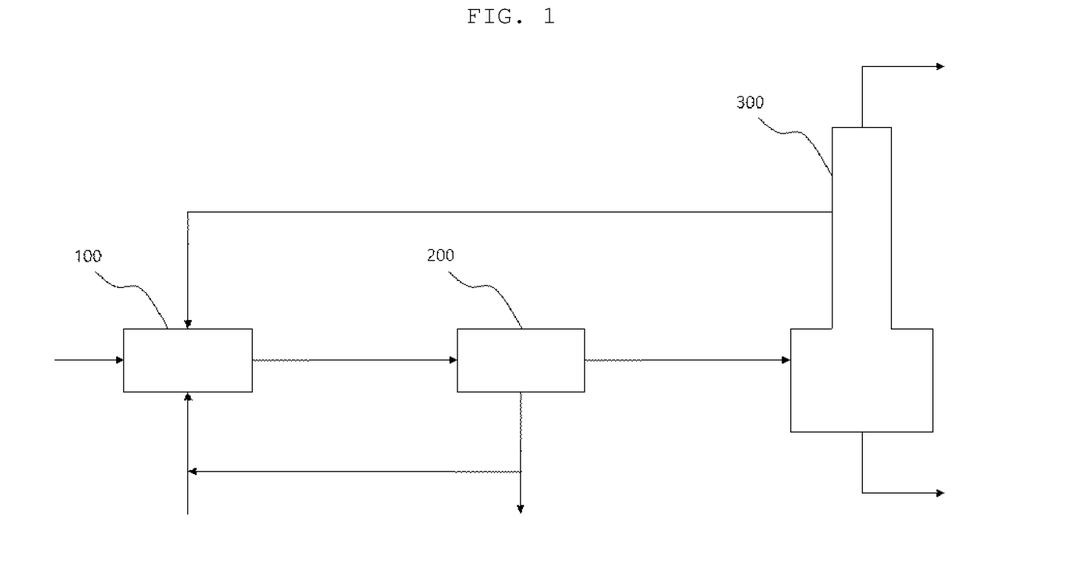
FIG. 1 is a process flow diagram of a method for decomposing a phenolic by-product according to an exemplary embodiment of the present invention.

A phenolic by-product was decomposed according to a process flow diagram illustrated in FIG. 1. Specifically, a mixed by-product stream of a composition shown in Table 1 and a decomposition apparatus 300 side discharge stream of a composition shown in Table 1 were fed to a mixing apparatus 100, and a process water stream was fed to the mixing apparatus 100 in a state where a pH of the process water stream was maintained at pH 4.

A flow rate ratio between the mixed by-product stream, the decomposition apparatus 300 side discharge stream, and the process water stream that were injected into the mixing apparatus 100 was 1:0.25:1.25 based on 1,000 kg/hr of the mixed by-product stream.

Thereafter, the mixture was left in a phase separation apparatus 200 for 0 hours, 3 hours, and 5 hours, and then a content of a salt in an oil phase obtained by phase separation and salt removal efficiency were measured. The results are shown in Table 2. In addition, compositions of a decomposition apparatus 300 top discharge stream decomposed in the decomposition apparatus 300 and discharged are shown in Table 3.

TABLE 1

| Classification | | Mixed by-product stream | Decomposition apparatus side discharge stream |
|---|---|---|---|
| Phenol | (wt %) | 4.85 | 19.87 |
| Alpha-methyl styrene | (wt %) | 7.14 | 5.92 |
| Cumene | (wt %) | 0.00 | 0.94 |
| Acetophenone | (wt %) | 11.60 | 46.75 |
| Isopropyl phenol | (wt %) | 0.00 | 26.19 |
| Cumylphenol | (wt %) | 15.32 | 0.00 |
| Alpha-methyl styrene dimer | (wt %) | 10.74 | 0.00 |
| Bisphenol A | (wt %) | 11.56 | 0.00 |
| Etc. | (wt %) | 38.79 | 0.33 |
| Total | (wt %) | 100.00 | 100.00 |

TABLE 2

| Classification | | Example 1 |
|---|---|---|
| Content of salt in oil phase after being left in phase separation apparatus for 0 hours | (ppm) | 380 |
| Content of salt in oil phase after being left in phase separation apparatus for 3 hours | (ppm) | 115 |
| Removal efficiency of salt in oil phase after being left in phase separation apparatus for 3 hours | (%) | 62 |
| Content of salt in oil phase after being left in phase separation apparatus for 5 hours | (ppm) | 35 |
| Removal efficiency of salt in oil phase after being left in phase separation apparatus for 5 hours | (%) | 75 |
| Thermal energy used per ton of mixed by-product | (Mcal/ton) | 68 |

TABLE 3

| Classification | | Example 1 |
|---|---|---|
| Phenol | (wt %) | 32.99 |
| Alpha-methyl styrene | (wt %) | 50.07 |
| Cumene | (wt %) | 11.83 |
| Acetophenone | (wt %) | 0.01 |
| Isopropyl phenol | (wt %) | 0.00 |
| Cumylphenol | (wt %) | 0.00 |
| Alpha-methyl styrene dimer | (wt %) | 0.00 |
| Bisphenol A | (wt %) | 0.00 |
| Etc. | (wt %) | 5.10 |
| Total | (wt %) | 100.00 |

COMPARATIVE EXAMPLES

Comparative Example 1

Figure 2:
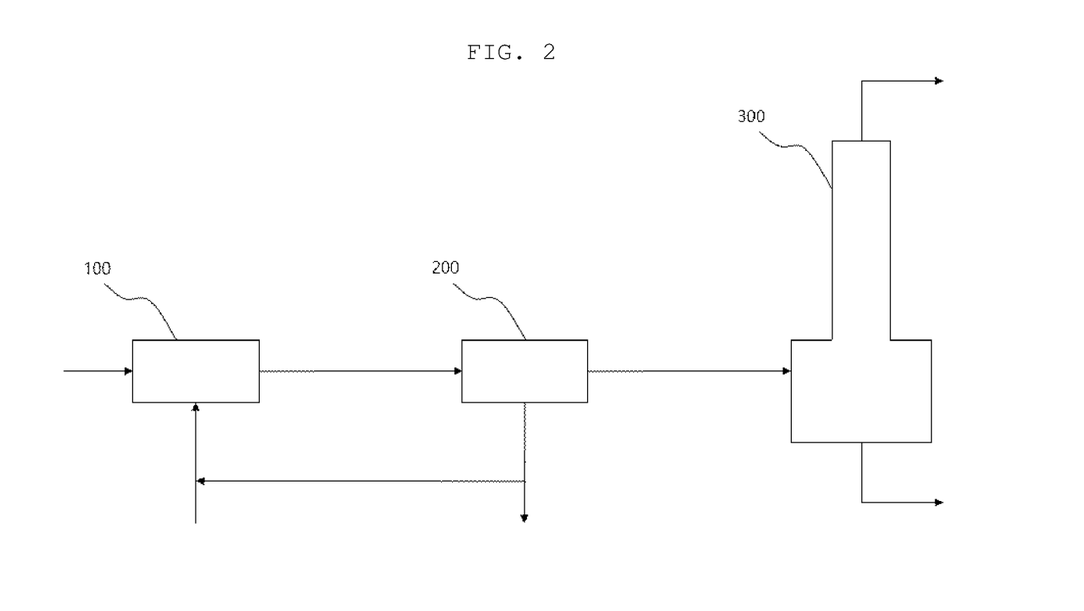
FIG. 2 is a process flow diagram of a method for decomposing a phenolic by-product according to Comparative Example 1.

A phenolic by-product was decomposed according to a process flow diagram illustrated in FIG. 2. Specifically, the process was performed in the same manner as that of Example 1, except that the decomposition apparatus 300 side discharge stream was not fed to the mixing apparatus 100. In addition, a flow rate ratio of the mixed by-product stream to the process water stream that were injected into the mixing apparatus 100 was 1:1 based on 1,000 kg/hr of the mixed by-product stream.

Thereafter, the mixture was left in the phase separation apparatus 200 for 0 hours, 3 hours, and 5 hours, and then a content of a salt in an oil phase obtained by phase separation and salt removal efficiency were measured. The results are shown in Table 4.

TABLE 4

| Classification | | Comparative Example 1 |
|---|---|---|
| Content of salt in oil phase after being left in phase separation apparatus for 0 hours | (ppm) | 380 |
| Content of salt in oil phase after being left in phase separation apparatus for 3 hours | (ppm) | 210 |
| Removal efficiency of salt in oil phase after being left in phase separation apparatus for 3 hours | (%) | 45 |
| Content of salt in oil phase after being left in phase separation apparatus for 5 hours | (ppm) | 210 |
| Removal efficiency of salt in oil phase after being left in phase separation apparatus for 5 hours | (%) | 45 |
| Thermal energy increased per ton of mixed by-product | (Mcal/ton) | — |

Comparative Example 2

Figure 3:
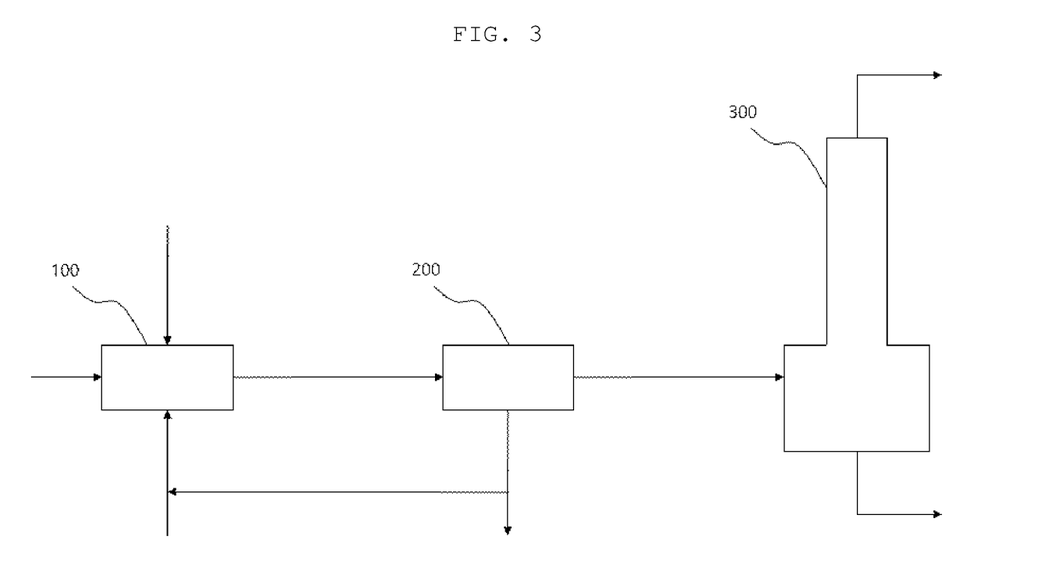
FIG. 3 is a process flow diagram of a method for decomposing a phenolic by-product including a phenol production process according to Comparative Examples 2 and 3.

A phenolic by-product was decomposed according to a process flow diagram illustrated in FIG. 3. Specifically, the process was performed in the same manner as that of Example 1, except that the decomposition apparatus 300 side discharge stream was not fed to the mixing apparatus 100, and a stream of a composition shown in Table 5 was fed to the mixing apparatus 100 as an organic matter of an acetone production column (APC) BTM separator.

In addition, a flow rate ratio between the mixed by-product stream, the APC BTM separator organic matter stream, and the process water stream that were injected into the mixing apparatus 100 was 1:0.25:1.25 based on 1,000 kg/hr of the mixed by-product stream.

Thereafter, the mixture was left in the phase separation apparatus 200 for 0 hours, 3 hours, and 5 hours, and then a content of a salt in an oil phase obtained by phase separation and salt removal efficiency were measured. The results are shown in Table 6.

TABLE 5

| Classification | | APC BTM separator organic matter |
|---|---|---|
| Phenol | (wt %) | 0.00 |
| Alpha-methyl styrene | (wt %) | 20.00 |
| Cumene | (wt %) | 80.00 |
| Acetophenone | (wt %) | 0.00 |
| Isopropyl phenol | (wt %) | 0.00 |
| Cumylphenol | (wt %) | 0.00 |
| Alpha-methyl styrene dimer | (wt %) | 0.00 |
| Bisphenol A | (wt %) | 0.00 |
| Etc. | (wt %) | 0.00 |
| Total | (wt %) | 100.00 |

TABLE 6

| Classification | | Comparative Example 2 |
|---|---|---|
| Content of salt in oil phase after being left in phase separation apparatus for 0 hours | (ppm) | 380 |
| Content of salt in oil phase after being left in phase separation apparatus for 3 hours | (ppm) | 50 |
| Removal efficiency of salt in oil phase after being left in phase separation apparatus for 3 hours | (%) | 84 |
| Content of salt in oil phase after being left in phase separation apparatus for 5 hours | (ppm) | 50 |
| Removal efficiency of salt in oil phase after being left in phase separation apparatus for 5 hours | (%) | 84 |
| Thermal energy increased per ton of mixed by-product | (Mcal/ton) | 111 |

Comparative Example 3

A phenolic by-product was decomposed according to the process flow diagram illustrated in FIG. 3. Specifically, the process was performed in the same manner as that of Example 1, except that the decomposition apparatus 300 side discharge stream was not fed to the mixing apparatus 100, and a decomposition apparatus 300 top discharge stream was fed to the mixing apparatus 100.

In addition, a flow rate ratio between the mixed by-product stream, the decomposition apparatus 300 top discharge stream, and the process water stream that were injected into the mixing apparatus 100 was 1:0.25:1.25 based on 1,000 kg/hr of the mixed by-product stream.

Thereafter, the mixture was left in the phase separation apparatus 200 for 0 hours, 3 hours, and 5 hours, and then a content of a salt in an oil phase obtained by phase separation and salt removal efficiency were measured. The results are shown in Table 7.

TABLE 7

| Classification | | Comparative Example 3 |
|---|---|---|
| Content of salt in oil phase after being left in phase separation apparatus for 0 hours | (ppm) | 380 |
| Content of salt in oil phase after being left in phase separation apparatus for 3 hours | (ppm) | 85 |
| Removal efficiency of salt in oil phase after being left in phase separation apparatus for 3 hours | (%) | 72 |
| Content of salt in oil phase after being left in phase separation apparatus for 5 hours | (ppm) | 65 |
| Removal efficiency of salt in oil phase after being left in phase separation apparatus for 5 hours | (%) | 79 |
| Thermal energy increased per ton of mixed by-product | (Mcal/ton) | 152 |

Referring to Tables 2 and 3, it could be confirmed that the bisphenol A by-product and the mixed by-product of the phenol by-products were decomposed by the method of decomposing of a phenolic by-product according to the present invention, such that the removal efficiency of the salt included in the mixed by-product was highly maintained and a yield of the active ingredient was high. In addition, it was confirmed that the consumption of the thermal energy was low.

On the other hand, referring to Table 4, it could be confirmed that in a case where a separate organic solvent was not fed to the mixing apparatus 100 instead of the decomposition apparatus 300 side discharge stream prior to the decomposition of the phenolic by-product, the salt removal efficiency was significantly reduced.

In addition, referring to Table 6, in a case where the APC BTM separator organic matter stream was fed to the mixing apparatus 100 instead of the decomposition apparatus 300 side discharge stream prior to the decomposition of the phenolic by-product, the salt removal efficiency was relatively high, but the cumene and the alpha-methyl styrene were required to be obtained as a product again, which causes an overload in the phenol purification process and the high consumption of the thermal energy in the decomposition apparatus 300.

In addition, referring to Table 7, in a case where the decomposition apparatus 300 top discharge stream was fed to the mixing apparatus 100 instead of the decomposition apparatus 300 side discharge stream prior to the decomposition of the phenolic by-product, the salt removal efficiency was relatively high, but the organic matters such as phenol, cumene, and alpha-methyl styrene discharged as the active ingredients were used as they were, and thus, the consumption of the thermal energy in the decomposition apparatus 300 was very high.

From the above results, the present inventors found that in a case where the mixed by-product of the phenolic by-product produced in the bisphenol A production process and the phenolic by-products produced in the phenol production process were decomposed according to the present invention, the salt included in the mixed by-product can be effectively removed prior to the decomposition of the mixed by-product, such that the active ingredient can be effectively obtained by decomposing the mixed by-product and the content of the acetophenone in the active ingredient can be reduced.

The invention claimed is:

1. A method of decomposing a phenolic by-product, the method comprising:
   a step S10 of injecting and mixing a mixed by-product stream of bisphenol A by-product produced in a bisphenol A production process and a phenol by-product produced in a phenol production process, a decomposition apparatus side discharge stream, and a process water stream in a mixing apparatus;
   a step S20 of injecting a mixing apparatus discharge stream discharged from the mixing apparatus into a phase separation apparatus and phase-separating the mixing apparatus discharge stream into an oil-phase stream and a liquid-phase aqueous solution stream;
   a step S30 of feeding the oil-phase stream, which is phase-separated in the step S20 and discharged from the phase separation apparatus, to a decomposition apparatus to decompose the oil-phase stream; and
   a step S40 of circulating the decomposition apparatus side discharge stream obtained by the decomposition in the step S30 to the mixing apparatus in the step S10.

2. The method of claim 1, wherein the mixed by-product stream includes one or more selected from the group consisting of bisphenol A, phenol, alpha-methyl styrene, acetophenone, cumylphenol, and alpha-methyl styrene dimer.

3. The method of claim 1, wherein the decomposition apparatus side discharge stream includes one or more selected from the group consisting of phenol, acetophenone, isopropyl phenol, alpha-methyl styrene, and cumene.

4. The method of claim 1, wherein the decomposition apparatus side discharge stream comprises acetophenone in an amount of 20 wt % or more.

5. The method of claim 1, wherein a pH of the process water is 3.5 to 7.

6. The method of claim 1, wherein the process water stream includes a process water derived from the liquid-phase aqueous solution stream, which is phase-separated in the step S20.

7. The method of claim 1, wherein a decomposition apparatus top discharge stream obtained by the decomposition in the step S30 includes one or more selected from the group consisting of phenol, alpha-methyl styrene, and cumene.

8. The method of claim 1, wherein in the step S10, a flow rate ratio of the mixed by-product stream to the decomposition apparatus side discharge stream is 0.8 to 1.2:0.1 to 0.4.

9. The method of claim 1, wherein in the step S10, a flow rate ratio between the mixed by-product stream, the decomposition apparatus side discharge stream, and the process water stream is 0.8 to 1.2:0.1 to 0.4:0.8 to 1.5.

10. The method of claim 1, wherein in the step S20, the phase-separation is performed for 1 hour to 10 hours.

* * * * *